United States Patent [19]

Kimsey

[11] Patent Number: 4,993,410
[45] Date of Patent: Feb. 19, 1991

[54] PROSTHETIC REMOVAL DEVICE

[76] Inventor: Timothy P. Kimsey, 14801 E. 44th St., Independence, Mo. 64055

[21] Appl. No.: 345,401

[22] Filed: May 1, 1989

[51] Int. Cl.⁵ .............................................. A61F 5/04
[52] U.S. Cl. ...................................... 606/100; 623/22
[58] Field of Search ............. 128/92 R, 92 V, 92 VT, 128/92 VP, 92 C, 92 CA, 92 EC, 83, 303 R; 403/256; 623/18, 22, 23

[56] References Cited

U.S. PATENT DOCUMENTS

| | | | |
|---|---|---|---|
| 757,195 | 4/1904 | Huff | 403/256 |
| 2,562,419 | 7/1951 | Ferris | 128/92 V |
| 3,208,450 | 9/1965 | Abelson | 128/92 VT |
| 3,626,935 | 12/1971 | Pollock et al. | 128/83 |
| 3,857,389 | 12/1974 | Amstutz | 128/92 VT |
| 4,153,053 | 5/1979 | Figallo | 128/92 |
| 4,222,382 | 9/1980 | Antonsson et al. | 128/303 |
| 4,248,232 | 2/1981 | Engelbrecht et al. | 128/305 |
| 4,459,985 | 7/1984 | McKay et al. | 128/92 VT |
| 4,462,395 | 7/1984 | Johnson | 128/92 |
| 4,475,549 | 10/1984 | Oh | 128/92 VP |
| 4,476,861 | 10/1984 | Dimakos et al. | 128/303 |
| 4,528,980 | 7/1985 | Kenna | 128/92 VP |
| 4,549,319 | 10/1985 | Meyer | 623/22 |
| 4,586,932 | 5/1986 | Scales | 623/16 |
| 4,642,121 | 2/1987 | Keller | 623/18 |
| 4,686,971 | 8/1987 | Harris et al. | 128/92 |
| 4,697,585 | 10/1987 | Gazale | 128/92 |
| 4,765,328 | 8/1988 | Keller et al. | 128/303 |

FOREIGN PATENT DOCUMENTS 1022328 3/1966 United Kingdom .......... 128/92 VT

Primary Examiner—Robert A. Hafer
Assistant Examiner—Charles H. Sam
Attorney, Agent, or Firm—Hovey, Williams, Timmons & Collins

[57] ABSTRACT

A surgical prothesis insertion and removal tool is provided which is particularly adapted for removing a variety of different prostheses by clamping to the stems thereof. The device hereof employs a force transmitting member, such as a slide hammer, which is mounted to a coupling member. The coupling member includes an opening adapted to receive a stem of the prosthesis therein, and preferably includes a series of differently sized sleeves which conform to respective stems of different prostheses. The coupling member is configured to clamp around the sleeve and stem, enabling the slide hammer to act to lift the coupling member and thereby remove the prostheses from a bone in which it had been originally placed.

20 Claims, 2 Drawing Sheets

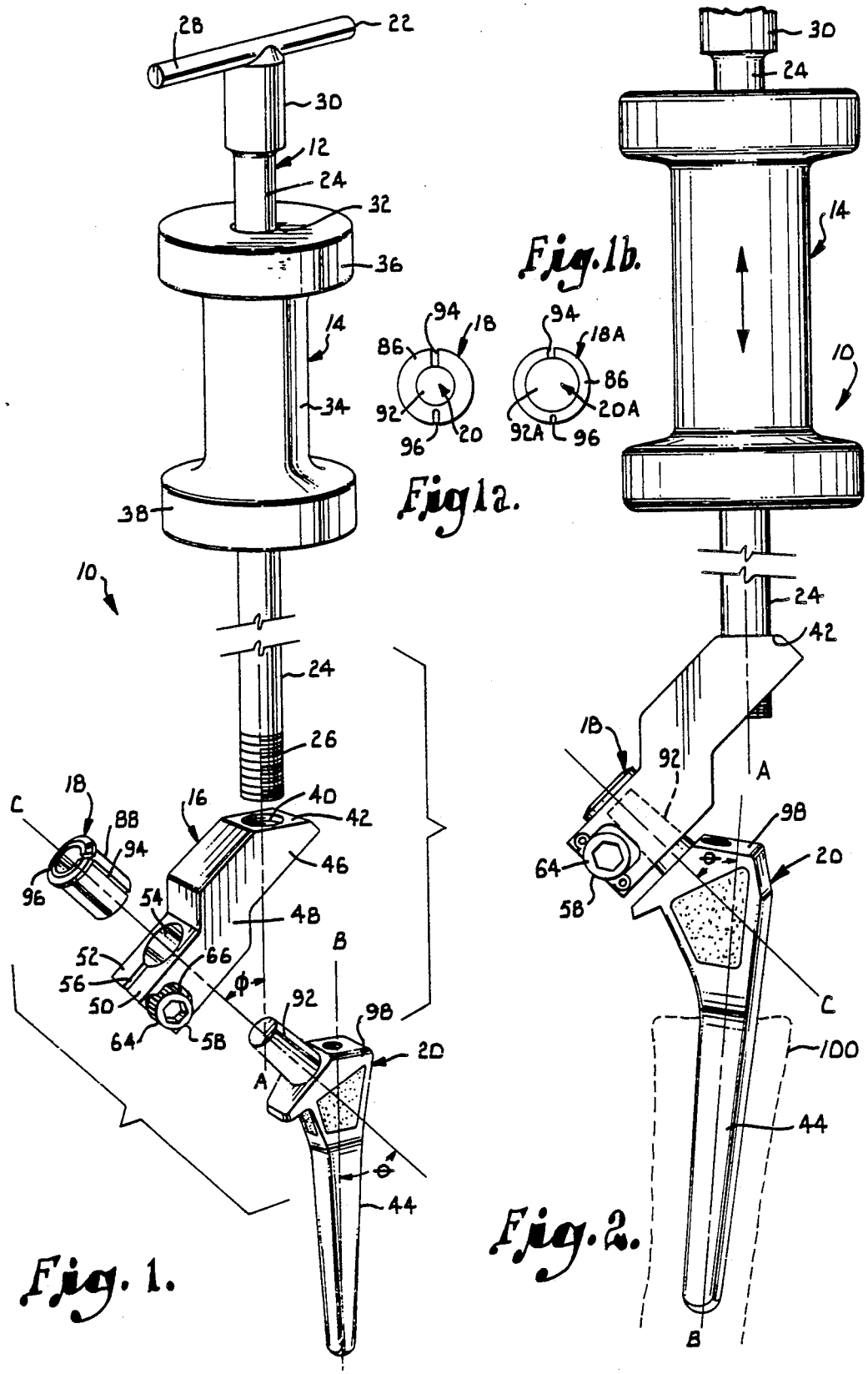

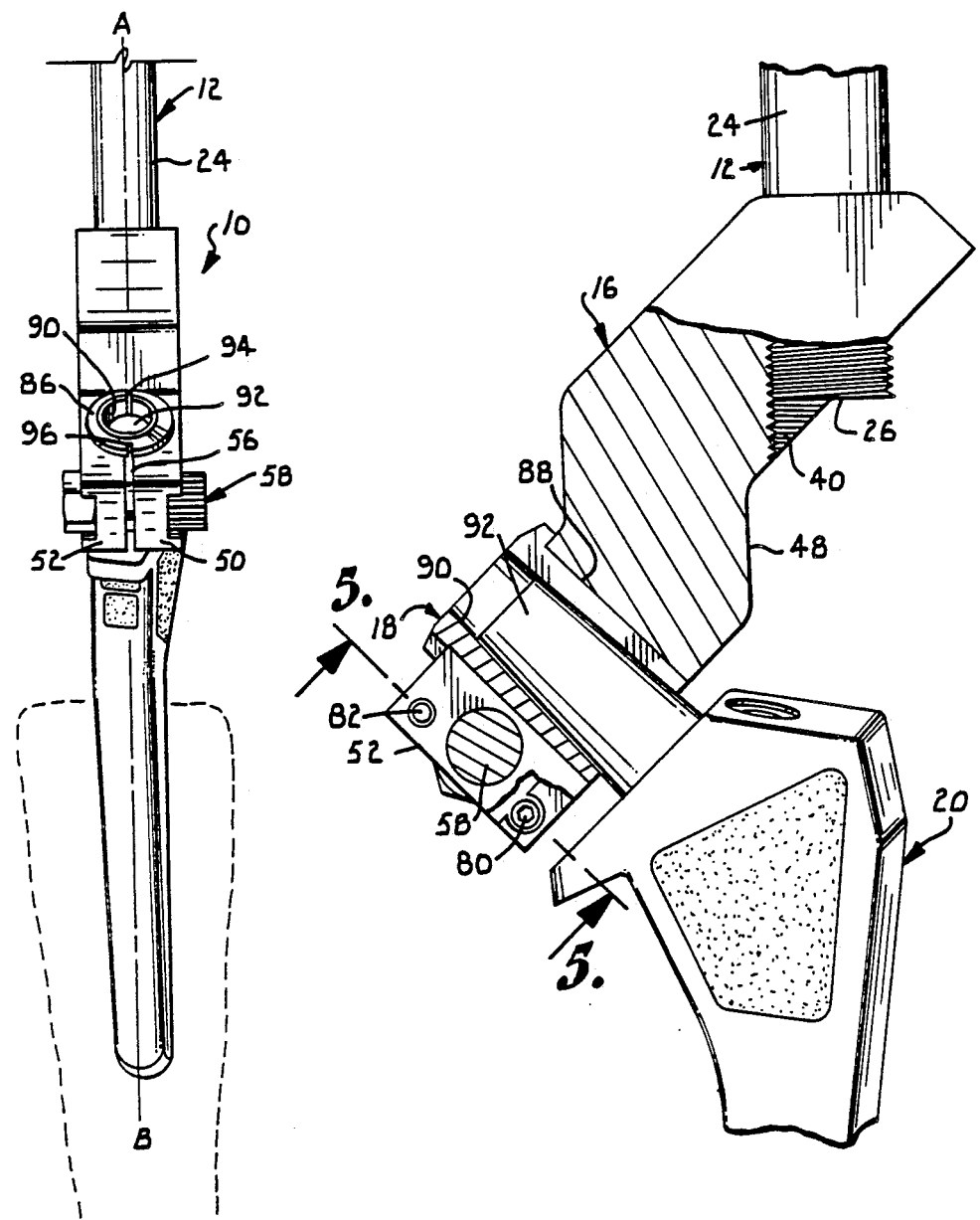

PROSTHETIC REMOVAL DEVICE

BACKGROUND OF THE INVENTION

1. Field of the Invention

This invention relates to a device for inserting and removing an orthopedic prosthesis during surgical operations. More particularly, it pertains to a device particularly adapted for attachment to a variety of different prostheses by direct attachment to a smooth sided stem thereof, permitting insertion and removal of the prosthesis without causing damage thereto.

2. Description of the Prior Art

The human body contains a number of joints between bones comprising the skeletal structure. These joints are often subject to continuous wear occasioned by the respective movement of the bones of the joint corresponding to flexure and relaxation of the associated muscles. Some joints, such as the hip, are subject to continuous and cyclical wear, with millions of cycles per year and occasional extreme shocks due to jumping, running, accidents or the like. Over time, the cartilage in the ball and socket joint of the hip may deteriorate to the point where an individual finds even normal walking extremely painful. When this occurs, a common surgical practice is the replacement of the hip joint by an artificial ball and socket joint. Of necessity, this includes the removal of a portion of the femur bone and insertion of a prosthesis therein.

Current surgical practices for inserting a prosthesis call for first creating a cavity for receipt of the prosthesis shank within the femur and then reaming out the cavity with a tool known as a broach to accommodate the specific prosthesis to be inserted. Because the broach and the prosthesis are specifically matched, the fit of the prosthesis in the femur bone is extremely tight. To accomplish a secure and tight fit, it is necessary to employ a tool to ensure that the prosthesis is tightly seated.

By the same token, it may be appreciated that after surgery, the bone and blood vessels surround the shank of the prosthesis and further tighten the fit between the prosthesis and the bone. This most desirable result ensures that the hip joint will function normally. However, on occasion the bone suffers further disease, injury or the like which may necessitate the removal of the prosthesis. In such circumstances, the secure fit of the prosthesis to the femur makes its removal extremely difficult.

This problem is compounded by two factors. First, each prosthesis manufacturer constructs its prostheses somewhat differently. While all tend to employ some type of smooth sided stem for receiving a spherically shaped ball thereon, each prosthesis may employ different tapers or other structure which makes it difficult to grasp the stem and remove the prosthesis without damage thereto.

It is to be further understood that each prosthesis is specially constructed and relatively expensive. Thus, it is especially desirous to avoid damage to the prosthesis, which may cost several thousand dollars each. Moreover, the force required to remove the prosthesis is substantial, in that the effect of the bone growth around the prosthesis tends to prevent its easy removal.

For these reasons, it has heretofore been difficult to easily and efficiently both insert and remove a variety of different prostheses with a single tool. Moreover, because of the various types of prosthesis on the market by different manufacturers, no single tool has been effective at removing a variety of different prostheses from different sources. Finally, a smooth sided stem being the only common portion of these different prostheses which projects above the femur, no single tool has been capable of grabbing different prostheses by the stem without damaging them.

SUMMARY OF THE INVENTION

The problems outlined above are in large measure solved by the present invention which provides a means whereby a surgeon may quickly insert or remove a prosthesis by grasping the prosthesis by the smooth sided stem projecting therefrom. The device hereof is especially useful in hip prosthesis surgery where substantial effort must be expended, the device hereof overcoming the natural tendency of the device to slip off the smooth sided stem of the prosthesis.

Broadly speaking, the preferred device hereof includes a coupling member for attachment to the prosthesis, a slide bar threadably engaged with the coupling member, and a weight slidable along the rod for imparting force for insertion or removal of the prosthesis during surgery. The bar is preferably oriented to be substantially parallel to the shank of the prosthesis inserted in the femur, whereby movement of the weight along the rod will be substantially in the same direction as the movement of the shank in and out of the femur. Yet further, the components are preferably made of stainless steel for cleanliness during the surgical operation and durability during repeated use. The coupling member preferably includes a sleeve for insertion therein, the sleeve being particularly adapted for use with a particular stem of a prosthesis. Thus, different sleeves may be substituted for different prostheses without the necessity of altering the other components.

In particularly preferred forms, the coupling device is provided with a bore for receiving the sleeve, the bore and coupling device being provided with a slot for tightening the coupling member around the sleeve. Furthermore, the sleeve is provided with a gap along one portion thereof whereby the sleeve itself may be tightened around the tapered stem. The inherent elasticity of the coupling device enables it to return to a somewhat spread condition when a clamping bolt is loosened, but additional expansion screws may be included for ease in removing the sleeve and coupling member from the prosthesis.

BRIEF DESCRIPTION OF THE DRAWING

FIG. 1 is a perspective, exploded view of the prosthesis insertion and removal device hereof, with the rod foreshortened, and the components positioned in relationship to a conventional hip prosthesis;

FIG. 1A is an angled elevation view looking along axis C showing stems of different prostheses and corresponding sleeves mated therewith;

FIG. 2 is a fragmentary side elevation view of the device hereof shown coupled to a prosthesis shown inserted in a femur bone, with the rod portion of the device foreshortened;

FIG. 3 is an fragmentary front elevation view of the device hereof;

FIG. 4 is an enlarged fragmentary side elevation view in partial sectional of the device hereof showing the insertion of the stem of the prosthesis into the sleeve, and showing the bolt and expansion screws in the jaws of the coupling member; and FIG. 5 is an enlarged, fragmentary section view along line 5—5 of FIG. 4, showing the positioning of the clamping bolt and the expansion screws in the jaws of the coupling member.

DETAILED DESCRIPTION OF THE DRAWING

Referring now to the drawing, a prosthetic removal device 10 in accordance with the present invention broadly includes a slide bar 12, sliding weight 14, coupling member 16 and sleeve 18, as shown in FIG. 1. The components are adapted to interconnect for insertion and removal of a prosthesis, such as prosthesis 20 shown herein. Prosthesis 20 shown in the drawing is of a type conventionally used in hip replacement surgery, but it may be appreciated that the present invention may be used with a variety of hip prostheses having a stem projecting therefrom or with other prostheses in other joint replacement surgery.

In more detail, prosthetic removal device 10 includes slide bar 12 having a handle 22 at one end thereof and a rod 24 having a threaded portion 26 at a second, opposed end thereof. The handle 22 includes cross member 28 which is graspable by a human hand, and head 30. The head 30 is axially aligned with rod 24 and of a somewhat greater cross-sectional dimension for reasons as will be set forth hereinafter. Rod 24 is substantially uniform along the length thereof and smooth sided for easy axial movement of weight 14 therealong.

Weight 14 may be of any particular configuration but is preferably dumbbell shaped, as shown in the drawing hereof. As may be seen from FIG. 1, weight 14 is preferably essentially tubular in construction, being provided with a central bore 32 extending therethrough. The weight is preferably between two and ten pounds, and a six pound weight has proven to work well with this device. The bore 32 is somewhat greater in diameter and complemental with rod 24 whereby weight 14 may be slidable along rod 24. However, bore 32 is preferably somewhat smaller than the transverse dimension of head 30. Weight 14 includes a graspable center section 34 between opposed hammerhead members 36 and 38.

Coupling member 16 includes an internally threaded hole 40 for receiving threaded portion 26 of rod 24 in threadable engagement therewith along axis A, as shown in FIG. 2. Hole 40 is circular in cross section and oriented along longitudinal axis A as shown in FIGS. 1 and 2. Axis A is substantially parallel to longitudinally extending axis B along which shank 44 of prosthesis 20 is aligned. Shoulder 42 surrounds hole 40 whereby hammerhead 38 may rest thereon or strike shoulder 42 in abutting engagement.

Coupling member 16 also includes arm portion 46, neck 48, and jaws 50 and 52 which are of a unitary construction, preferably made of stainless steel. Jaws 50 and 52 surround opening 54 which is oriented along axis C as shown in FIGS. 1 and 2. Axis C is oriented at an oblique angle phi to axis A as shown in FIG. 1, angle phi being roughly equivalent to angle theta between axis B and axis C, as shown in FIG. 2. Angle theta and angle phi are between 40 and 65', and preferably in the range of 50 to 55'.

Jaws 50 and 52 define gap 56 therebetween, gap 56 extending through to opening 54, thereby permitting resilient jaw members 50 and 52 to open or close, thereby permitting opening 54 to constrict or expand.

As may be seen from FIG. 3, gap 56 completely separates jaw members 50 and 52 at the end of coupling device 16 distal from hole 40.

Jaws 50 and 52 are operably interconnected by a threaded, clamping cross bolt 58 extending transversely through each of jaws 50 and 52. As may be seen in FIG. 5, cross bolt 58 includes threaded section 62 and ribbed Allen head 64, adapted for receiving an Allen head wrench in engagement therewith. Ribbed Allen head 64 is free to rotate within recess 66 of coupling member 16. Opposed to Allen head 64 is hex nut 68 which is also received within a corresponding recess 70 of coupling member 16. However, at least one face 72 of hex nut 68 remains in engagement with the portion of coupling member 16 surrounding recess 70 whereby nut 68 is not free to rotate. Thus, cross bolt 58 may move transversely when rotated while hex nut 68 remains in a fixed position while threadably engaged to cross bolt 58, as shown in FIG. 5.

Each jaw member 50 and 52 also includes two small theaded holes 74 and 76. The holes 74 and 76 receive Allen head expansion screws 78, 80, 82 and 84 therein in threaded engagement. As may be seen in FIG. 5, when the screws are turned by an Allen wrench or the like in a clockwise direction, they move toward the gap 56 and thus the opposing expansion screw, while when rotated in a counterclockwise direction, the screws 78, 80, 82 and 84 move away from the gap and thus away from the opposing expansion screw, thereby permitting resilient jaws 50 and 52 to return to a first, unbiased position.

The prosthetic removal device 10 hereof also includes a plurality of sleeves 18, as shown in FIG. 1. Each sleeve is substantially cylindrical in outside configuration and of an outside diameter complementary to opening 54 of coupling member 16. Each of the sleeves 18 includes a rim 86 above a barrel portion 88 of preferably constant outside diameter. The inner surface 90 of each sleeve is generally frustoconical and preferably tapered for complementary fit with stem 92 of prosthesis 20. In this regard, it is to be understood that the stems 92 are commonly tapered, and most often are of a smaller taper such as a Morse, Brown & Sharp, or Jarno taper, and best results are realized when these smaller, self-holding tapers are employed. However, the present device may also be used when the stems are of larger tapers. The barrel 88 and rim 86 is provided with a continuous slit 94 extending longitudinally through the barrel and rim of the sleeve 18, while a notch 96 extends into the rim 86 in opposed relationship to the slit 94.

As may be seen from FIG. 1A, various sleeves 18 and 18A may be employed to provide a precise fit with a corresponding stem 92 and 92A of different prostheses 20 and 20A. While hip prostheses may vary in configuration a design of the body 98 interconnecting stem 92 and shank 44, they commonly have a tapered stem 92 and elongated shank 44. A plurality of different sleeves 18 and 18A may be selectively and alternately inserted in opening 54 to engage a respective stem in surrounding, circumscribing relationship.

In operation, the prosthesis removal device 10 hereof is first assembled by sliding weight 14 onto slide bar 12 and then threading slide bar 12, which includes rod 24 and threaded portion 26, into hole 40 of coupling member 16 to provide a means of transmitting force along axis A.

An appropriate sleeve 18 corresponding to stem 92 is selected and inserted into opening 54 by direct insertion or, if the opening must be expanded in order to easily receive sleeve 18 therein, expansion screws 78, 80, 82 and 84 may be rotated in a clockwise direction. When the expansion screws 78, 82, 80 and 84 are turned after engagement, the jaws 50 and 52 spread apart to expand the opening, thus permitting freer insertion of sleeve 18 into coupling member 16. Thereafter, Allen screws 78, 80, 82 and 84 may be rotated in a counterclockwise direction, enabling cross bolt 58 to be rotated clockwise respective to hex nut 68 for closure of the jaws to grip sleeve 18 tightly within bore 54.

However, prior to final tightening of cross bolt 58 by use of an Allen wrench or the like, prosthetic removal device 10 is positioned so that stem 92 is inserted within sleeve 18 so that stem 92 engages and is substantially enclosed within inner surface 90 of sleeve 18. Once fully inserted, as shown in FIGS. 2, 3 and 4, cross bolt 58 is rotated in a clockwise direction (when threads on the cross bolt are conventional clockwise threads). In this manner, the slit 94 enables the sleeve 18 to close tightly around the stem 92 of the prosthesis in circumscribing clamping arrangement thereby transmitting the clamping force substantially equally around the surface of stem 92.

Thereafter, the rod 24 of the prostehtic removal device 10 hereof should be in substantially parallel alignment with shank 44 of the prosthesis 20. The physician may then grasp the weight and slide the weight 14 rapidly along rod 24. The upward movement of the weight 14, upon striking head 30, causes the prosthesis to transmit an upward lifting force on the shank 44 of the prosthesis 20 which may be embedded in a femur 100 or other bone of a patient. Through repeated abutting engagement of the weight 14 with the head 30, the prosthesis 20 is urged upward and out of the femur 98 in which it had been held.

It may be appreciated from the foregoing that two important factors are related to the successful removal of a prosthesis without damaging the stem 92 thereof. The first is the complementary engagement of the respective sleeve 18 with the stem 92 of the prosthesis whereby jaws 50 and 52 may be tightened by Allen bolt 64 to narrow slit 94 during compression. By virtue of the fact that the sleeve lies in surrounding relationship all around the stem, it engages no specific point thereof to a greater extent than any other point around its circumference. The sleeve 18 may thus be tightened around the stem without damaging it. The second important factor in ensuring proper removal of the prosthesis 20 through the device 10 hereof is the angular relationship of the slide bar 14 to the opening 54 and sleeve 18, shown by the angle theta. Weight 14 may be moved along axis A which will be substantially parallel to axis B in which shank 44 of prosthesis 20 lies. Because the sleeve 18 grips the stem 92 along axis C at an oblique angle to axis A, the force transmitted by upward movement of the weight 14 does not cause the sleeve 18 to slip off stem 92, but rather the inner surface 90 remains in gripping relationship to stem 92.

After removal of the prosthesis 44, the Allen bolt 58 may be rotated in a counterclockwise direction to loosen the grasp of the jaws 50 and 52 on the sleeve 18, and if further assistance is needed to remove the sleeve, expansion screws 78, 80, 82 and 84 may be rotated in respective clockwise directions in order to force apart jaws 50 and 52 and expand jaws 50 and 52, further relaxing the hold of sleeve 18 on stem 92 and releasing sleeve 18 from coupling device 16.

It should also be understood that device 10 hereof is useful for insertion of orthopedic prostheses as well. After the necessary cavity in the femur 100 has been created by a broach to receive shank 44 therein, the prosthesis 20 may be coupled to the device 10 hereof for insertion. That is to say, stem 92 may be inserted into its respective sleeve 18 whereby the shank 44 is aligned along axis B substantially coaxially with axis A of rod 24. Thereafter, prosthesis 20 may be placed in the cavity in the femur 100, and driven to the desired point of insertion by successive downward strokes of weight 14 which is slidably engaged with rod 24. On the downward strokes, weight 14 engages shoulder 42 surrounding hole 40, thereby creating an impact which urges shank 44 downward into final and proper placement within the femur 100. The device 10 may thereupon be removed from prosthesis 20 by rotating cross bolt 58 in a counterclockwise direction (as hex nut 68 is maintained in a fixed position within recess 70), the complementary frustoconical tapers of stem 92 and frustoconical inner surface 90 of the sleeve permitting easy separation therebetween. Therafter, if necessary to remove sleeve 18 from coupling member 16, the four expansion screws 78, 80, 82 and 84 may each be rotated in a respective clockwise direction by an Allen wrench whereupon the jaws 50 and 52 may be spread to loosen the grasp of jaws 50 and 52 on sleeve 18 and permit it to be removed from opening 54.

The device hereof may be machined or cast, preferably of stainless steel, in order to provide the maximum resistance to rust which is important, considering that such tools are used in a surgical theater and may be cleaned by steam under pressure to provide an antiseptic environment for surgery. Yet furthermore, it should be understood that a number of sleeves such as 18 and 18A, may be provided which have a rim 86 and the outside surface of barrel 88 of a common dimension, but that the inner surface 90 of each of the sleeves 18 will be cast or machined to attach to a specific size, taper or stem configuration of a particular stem 92.

I claim:

1. A prosthesis manipulation advice adapted for attachment to a surgical prosthesis having an elongated shank defining a first longitudinal axis, an elongated smooth-sided, tapered connection stem located opposite said shank and defining a second longitudinal axis oriented at an oblique angle relative to the first axis, said first axis comprising:

an elongated, force-transmitting element; and
means for releasably securing said element to said prosthesis for manipulation of the latter, including—
coupling means having structure defining a stem-receiving opening therein;
a sleeve disposed within said opening and presenting a smooth-sided tapered inner surface complemental with the stem for clamping engagement with said stem;
means for operatively clamping said opening-defining structure and said sleeve to said stem; and
means for operatively interconnecting said element and said coupling means with the longitudinal axis of the element being generally parallel with said first longitudinal axis, whereby axial forces transmitted through said element will affect manipulation of said prosthesis.

2. A prosthesis manipulation device as set forth in claim 1, there being a plurality of differently configured sleeves respectively and alternately disposable within said opening, said sleeve being selected from said plurality thereof.

3. A prosthesis manipulation device as set forth in claim 1, said sleeve including a slit extending longitudinally therealong for circumscribing closure of said sleeve around said stem.

4. A prosthesis manipulation device as set forth in claim 3, said means for spreading said jaws comprising at least one pair of opposed expansion screws.

5. A prosthesis manipulation device as set forth in claim 2, said sleeve including structure defining a longitudinally extending slit for enabling relative opening and closing thereof during clamping by said clamping means.

6. A prosthesis manipulation device as set forth in claim 1, said opening-defining structure including first and second jaw members.

7. A prosthesis manipulation device as set forth in claim 6, said clamping means including a clamping member extending through said jaws and oriented transversely to said opening for closing said first and second jaw members.

8. A prosthesis manipulation device as set forth in claim 7, including means for spreading said first and second jaw members.

9. A prosthesis manipulation device as set forth in claim 2, said opening being oriented at an oblique angle to both said first longitudinal axis and said second longitudinal axis.

10. A prosthesis manipulation device as set forth in claim 9, each of said sleeves having a substantially frustonconical inner surface.

11. A prosthesis manipulation device as set forth in claim 9, said connecting means including a transversely extending clamping member for selectively constricting the size of said opening.

12. A prosthesis manipulation device as set forth in claim 11, said connecting means including means for selectively expanding the size of said opening.

13. A prosthesis manipulation device as set forth in claim 12, said size expanding means comprising at least one member in threaded engagement with said connecting means.

14. A prosthesis manipulation device for use in handling a surgical prosthesis having an elongated shank defining a first longitudinal axis, an elongated, smooth-sided tapered connection stem located along a second longitudinal axis obliquely angled relative to said first longitudinal axis, said device comprising:
an elongated, force-transmitting element;
means for releasably securing said element to a prosthesis for manipulation of the latter, including
coupling means defining a smooth-sided, tapered, stem-receiving opening complemental with the prothesis stem therein for transmitting clamping force to the prosthesis stem in substantially circumscribing relationship; and
means remotely located from said force-transmitting element for imparting clamping force to said coupling means.

15. A prosthesis manipulation device as set forth in claim 14 wherein said stem-receiving opening is configured to present a tapered inner surface of complimentary configuration to said stem.

16. A prosthesis manipulation device as set forth in claim 15, wherein said coupling means includes at least one removable sleeve for mating engagement with said stem.

17. A device for use in manipulating a prosthesis having an outwardly projecting, smooth-sided stem tapering toward the distal end thereof, said device comprising:
a force transmitting element for imparting prosthesis manipulating force; and
coupling means for coupling said element with a prosthesis in order to transfer manipulating force thereto, said coupling means including—
means for operably connecting with said element,
gripping means including shiftable walls defining a smooth-sided, tapered, stem-receiving opening complemental with the prosthesis stem for selectively engaging the stem in a substantially circumscribing, gripping relationship, and
shifting means for selectively shifting said walls into said gripping relationship with the prosthesis stem in order to couple with and transfer manipulating force to the prosthesis by way of the prosthesis stem.

18. The device as set forth in claim 17, the prosthesis including a shank portion presenting a first axis, the stem presenting a second axis at an oblique angle relative to said first axis, said element presenting a longitudinal axis, said coupling means including means for coupling said element with the prosthesis in order to present said longitudinal axis in a generally parallel relationship with said first axis.

19. The device as set forth in claim 17, said gripping means including a replaceable sleeve presenting said shiftable walls.

20. The device as set forth in claim 19, said gripping means including a shiftable clamping portion defining a sleeve-receiving aperture for receiving said sleeve.

* * * * *

UNITED STATES PATENT AND TRADEMARK OFFICE
CERTIFICATE OF CORRECTION

PATENT NO. : 4,993,410

DATED : February 19, 1991

INVENTOR(S) : Timothy P. Kimsey

It is certified that error appears in the above-identified patent and that said Letters Patent is hereby corrected as shown below:

On the title page;

| | |
|---|---|
| Block 54, | change "PROSTHETIC REMOVAL DEVICE" to --PROSTHESIS MANIPULATION DEVICE--. |
| Block 76, | Inventor, add --William W. Bohn, 6720 Willow Lane, Mission Hills, Kansas 66208--. |
| Col. 2, Lines 57-59 | change: "stems of different prostheses and corresponding sleeves" to --a stem of a prosthesis and a corresponding sleeve--, and add a new paragraph after "mated therewith;" --Fig. 1b is an angled elevation view looking along axis C showing a stem of a different prosthesis and a corresponding sleeve mated therewith;--. |
| Col. 4, Line 50 | after "fig. 1A" add --and Fig. 1B--. |
| Col. 5, Line 34 | after "femur" change "98" to --100--. |
| Col. 6, Line 42 | change "advice" to --device--. |

Signed and Sealed this

Thirteenth Day of October, 1992

Attest:

DOUGLAS B. COMER

Attesting Officer

Acting Commissioner of Patents and Trademarks